(12) United States Patent
Smith et al.

(10) Patent No.: US 10,398,486 B2
(45) Date of Patent: Sep. 3, 2019

(54) ARTICULATING WIRE PASSER

(71) Applicants: Judd Michael Smith, Lebanon, NH (US); Tadd Nicholas Smith, Rye, NH (US); C Daniel Smith, St. Joseph, MO (US)

(72) Inventors: Judd Michael Smith, Lebanon, NH (US); Tadd Nicholas Smith, Rye, NH (US); C Daniel Smith, St. Joseph, MO (US)

( * ) Notice: Subject to any disclaimer, the term of this patent is extended or adjusted under 35 U.S.C. 154(b) by 28 days.

(21) Appl. No.: 15/627,777

(22) Filed: Jun. 20, 2017

(65) Prior Publication Data

US 2018/0360517 A1 Dec. 20, 2018

(51) Int. Cl.
*A61B 17/88* (2006.01)
*A61B 17/17* (2006.01)
*A61B 17/82* (2006.01)

(52) U.S. Cl.
CPC ...... *A61B 17/8861* (2013.01); *A61B 17/1796* (2013.01); *A61B 17/82* (2013.01)

(58) Field of Classification Search
CPC .............. A61B 17/885; A61B 17/8869; A61B 17/0469; A61B 17/0482; A61B 17/0483; A61B 17/8861; A61B 17/82; A61B 17/823; A61B 17/7053; A61B 17/842
USPC .......................................... 606/103, 144–150
See application file for complete search history.

(56) References Cited

U.S. PATENT DOCUMENTS

| | | | |
|---|---|---|---|
| 3,060,972 A | 10/1962 | Sheldon | |
| 5,810,832 A | 9/1998 | Blasingame et al. | |
| 5,851,209 A * | 12/1998 | Kummer | A61B 17/8861 606/103 |
| 5,921,918 A | 7/1999 | Riza | |
| 2006/0258951 A1* | 11/2006 | Bleich | A61B 17/1626 600/546 |
| 2006/0293691 A1* | 12/2006 | Mitra | A61B 17/8861 606/103 |
| 2007/0185532 A1* | 8/2007 | Stone | A61B 17/0401 606/232 |
| 2011/0295065 A1 | 12/2011 | Gurusamy et al. | |
| 2012/0215234 A1 | 8/2012 | Chowaniec et al. | |
| 2012/0232567 A1* | 9/2012 | Fairneny | A61B 17/0469 606/147 |
| 2013/0110134 A1 | 5/2013 | Pratt et al. | |
| 2014/0249530 A1 | 9/2014 | Babikian et al. | |
| 2015/0313656 A1* | 11/2015 | Hulliger | A61B 17/823 606/74 |
| 2016/0199057 A1 | 7/2016 | Parsons et al. | |

* cited by examiner

*Primary Examiner* — Julianna N Harvey
*Assistant Examiner* — Christina NegrelliRodriguez
(74) *Attorney, Agent, or Firm* — Hovey Williams LLP

(57) ABSTRACT

An articulating wire passer for passing a surgical wire around a bone broadly comprises a handle, rigid guide section, support guide, trigger, push rod, articulable member, tensioner, and wire catcher. The articulable member includes a number of pivotable segments configured to be advanced from an extended position to an engaged position via ratcheting action between the trigger and push rod. Tension in the surgical wire induced by the tensioner causes the pivotable segments to pivot as they advance from the rigid guide section and thus draw the surgical wire around the bone. The wire catcher allows the user to retrieve the surgical wire from the articulable member on the other side of the bone.

20 Claims, 3 Drawing Sheets

ARTICULATING WIRE PASSER

BACKGROUND

Bone fractures such as subtrochanteric and periprosthetic fractures often require surgery in which a bone brace or splint is attached to two or more fractured bone segments via surgical wire. Surgical wire passers are often used for guiding the surgical wire around the bone segments. Unfortunately, conventional surgical wire passers are unwieldy and often cause significant blood loss and soft tissue trauma as they are maneuvered around the bone. This is particularly exacerbated with large, unhealthy, and frail patients in which extra or extremely delicate soft tissue must be handled. The prolonged operation time increases post-operative morbidity and mortality. Furthermore, orthopedic trauma surgery is often conducted during evening hours or on weekends with inexperienced or overworked hospital staff, thus increasing the chances of inadvertent surgical complications resulting from the use of conventional surgical wire passers.

SUMMARY

Embodiments of the present invention solve the above-described problems and provide a distinct advance in surgical tools. An embodiment of the invention is an articulating wire passer broadly comprising a handle, a rigid guide section, a support guide, a trigger, a push rod, an articulable member, a tensioner, and a wire catcher.

The handle allows a user to grip the articulating wire passer and direct the articulable member towards a bone. The handle may have a pistol grip shape, a T-shape, or any other suitable shape and may have a protrusion, ergonomic gripping contours, ridges, or other geometry for allowing the user to firmly grasp the articulating wire passer.

The rigid guide section includes a channel, a number of forward facing ratchet teeth, and a ratchet guide. The channel guides the push rod and articulable member and is an open-topped U-shaped or C-shaped chute. The forward facing ratchet teeth are aligned with the channel for engaging a pawl of the push rod. The ratchet guide is configured to receive a guide pin of a pawl of the trigger and is a groove, slot, cam, or similar feature for allowing the pawl of the trigger to pivot into engagement with ratchet teeth of the push rod and shift the push rod forward.

The support guide has a curved front surface and a rear tip guide. The support guide abuts the bone and the tip guide directs the end segment of the articulable member towards the wire catcher after the end segment passes around the bone.

The trigger allows the user to advance the articulable member from an extended position to an engaged position and includes a return spring and a pawl. The return spring is connected between the trigger and the handle for urging the trigger to a released position when a squeezing force is removed from the trigger and handle. The pawl is configured to ratchetably engage ratchet teeth of the push rod and includes a guide pin or similar feature for following the ratchet guide of the rigid guide section and a release for disengaging the pawl from the ratchet teeth of the push rod. The trigger is pivotably connected to the handle near a top of the trigger so as to form a fulcrum point such that the squeezing force urges the pawl against the ratchet teeth of the push rod.

The push rod is an elongated member including a number of rear-facing ratchet teeth and a pawl. The rear-facing ratchet teeth are configured to be engaged by the pawl of the trigger. The pawl of the push rod is configured to engage the forward-facing ratchet teeth of the rigid guide section and may include a release for disengaging the pawl from the forward-facing ratchet teeth. The push rod is pivotably connected to the first segment of the articulable member at a distal end of the push rod.

The articulable member guides the surgical wire around the bone and comprises a number of segments pivotably connected to each other. The segments each include opposing top and bottom sides and opposing aft and forward ends. The forward ends are pivotably connected to aft ends of adjacent segments via pivot points on the top sides and are indented or stepped for interconnecting with adjacent segments to enhance lateral stability. A first end segment is pivotably connected to the distal end of the push rod. The distal end segment has a concave curved bottom side for following a convex contour of the bone and a convex curved top side. That is, the distal end segment is tapered for allowing the articulable member to be directed between the bone and non-skeletal body mass near the bone and pointed for penetration through fascial tissues. The end segment also has geometry for retaining an end stopper of the surgical wire therein. The segments and the push rod cooperatively form a longitudinal wire passageway configured to receive the surgical wire therein.

The tensioner includes a tensioning spring and a wire lock. The tensioning spring exerts a tensioning force on the surgical wire and is interchangeable for replacing a worn-out spring or for changing the amount of tension applied to the surgical wire for different applications. The wire lock engages the surgical wire and is a pivotable friction cam, clamp, or other similar locking mechanism.

The wire catcher includes a latch configured to engage the end of the surgical wire and a protrusion for allowing the user to push the wire catcher towards the tip guide and pull the wire catcher backwards after it catches the surgical wire. The wire catcher is slideably attached to an underside of the rigid guide section of the handle.

In use, the surgical wire is inserted through the wire passageway of the push rod and articulable member such that the end stopper of the surgical wire is retained by the end stopper engaging geometry of the end segment. The tensioning spring of the tensioner is optionally pre-compressed a desired amount. The wire lock is then shifted into engagement with the surgical wire regardless of whether the tensioning spring has been pre-compressed. The articulating wire passer is then positioned such that the curved surface of the support guide rests against the bone.

The trigger is then squeezed such that the pawl of the trigger urges the push rod and articulable member forward a small amount along the channel of the rigid guide section via the ratchet teeth of the push rod. That is, the pawl of the push rod passively slides over the ratchet teeth of the rigid guide section as the push rod is moved forward and engages one of ratchet teeth when the push rod and articulable member stop advancing, which prevents the push rod and articulable member from backtracking.

The end segment of the articulable member pulls the surgical wire and hence the wire lock forward via the end stopper engaging geometry. This compresses the tensioning spring, which induces or increases tension in the surgical wire. The tension in the surgical wire causes segments to pivot relative to adjacent segments around the bone as they emerge from the distal end of the channel. The free segments may pivot to a predetermined relative angle dictated by the shape of the segments or a desired relative angle according to a wire tension induced by the tensioner.

The trigger is then released such that the return spring urges the trigger back to a relaxed position. The pawl of the trigger passively slides over the ratchet teeth of the push rod as the trigger returns to the relaxed position and engages one of the ratchet teeth when the trigger is stopped or reaches the relaxed position. The trigger is repeatedly squeezed and released such that the articulable member curls around the bone from an extended position to an engaged position as the articulable member and push rod are ratcheted forward.

The end segment pierces and/or passes between soft tissues and draws the surgical wire around the bone as the articulable member advances. The end section then advances along the tip guide of the support guide towards the wire catcher on the other side of the bone.

The wire catcher is then shifted forward along the underside of the rigid guide section until the latch has moved past the end stopper of the surgical wire. The wire catcher is then shifted backwards along the underside of the rigid guide section such that the latch engages the end stopper of the surgical wire. Alternatively, the latch may automatically engage the end stopper when the wire catcher is shifted forward.

The release of the trigger is then depressed or rotated to disengage the pawl of the trigger from the ratchet teeth of the push rod and the release of the push rod is depressed or rotated to disengage the pawl of the push rod from the ratchet teeth of the rigid guide section. The push rod and articulable member are then shifted backwards towards the tensioner such that the segments shift back around the bone from the engaged position to the extended position. The surgical wire stays wrapped around the bone because the end stopper of the surgical wire is in engagement with the latch of the wire catcher. The surgical wire is then clamped to form a construct that encircles the bone, which can be used alone or in combination with plates, rods, or other methods of bone fixation. The articulating wire passer is then repositioned laterally along the bone for passing additional surgical wire around the bone.

The above-described articulating wire passer provides several advantages over conventional wire passers. For example, the articulable member curls around the bone due to tension in the surgical wire, thus ensuring that the disturbance of non-skeletal body mass near the bone is minimized. The articulating wire passer also allows the surgical wire to be passed around the bone without the handle being moved significantly within the operating area. This reduces the surgical exposure and total space required to complete the surgery and reduces the likelihood of damaging non-skeletal body mass. The support guide allows the user to position the articulating wire passer against the bone properly before passing the surgical wire around the bone, which increases repeatability and accuracy of the procedure while decreasing the amount of time required to complete the surgery.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the preferred embodiments and the accompanying drawing figures.

Figure 1:
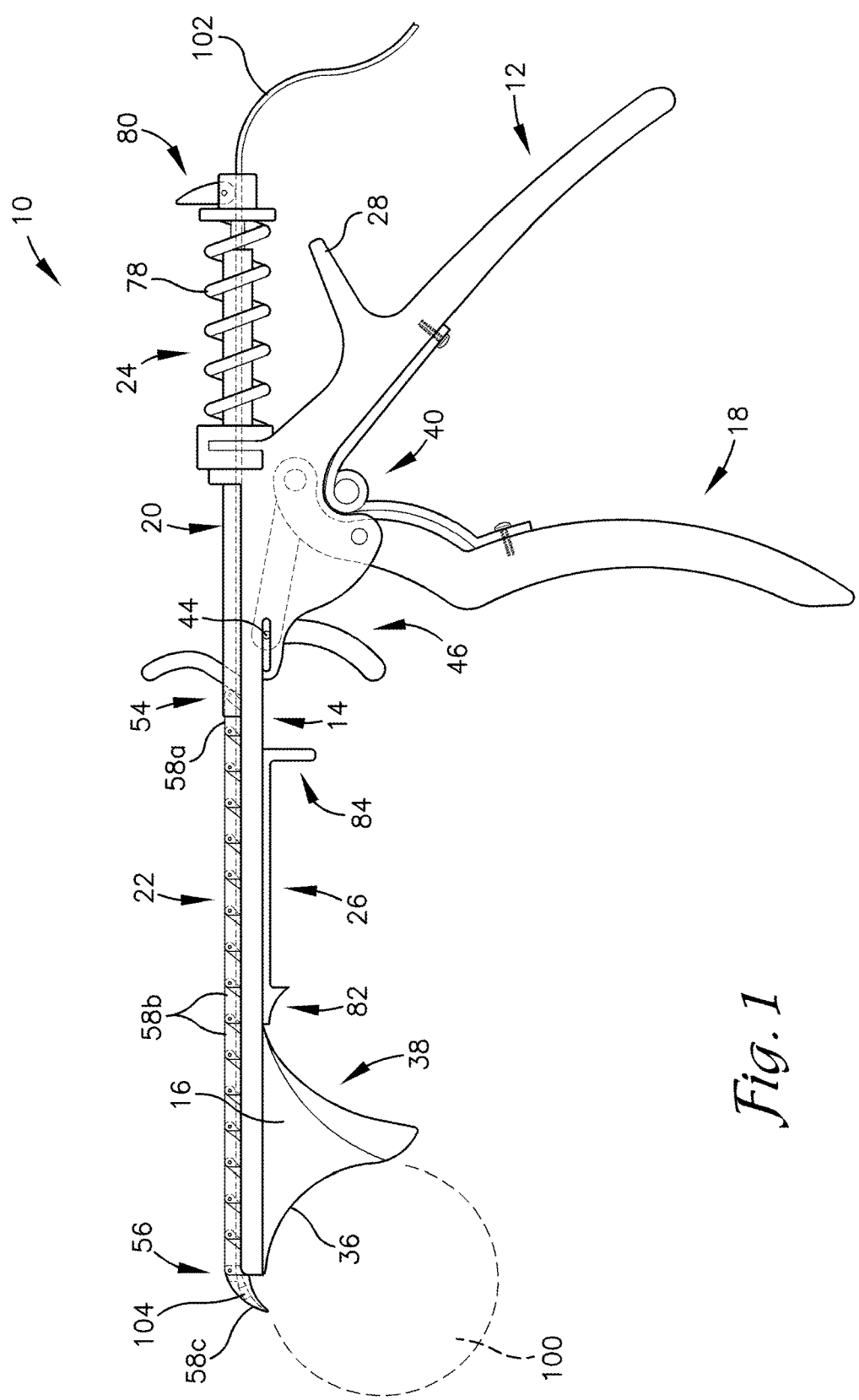
FIG. 1 is a side elevation view of an articulating wire passer constructed in accordance with an embodiment of the invention.
Figure 2:
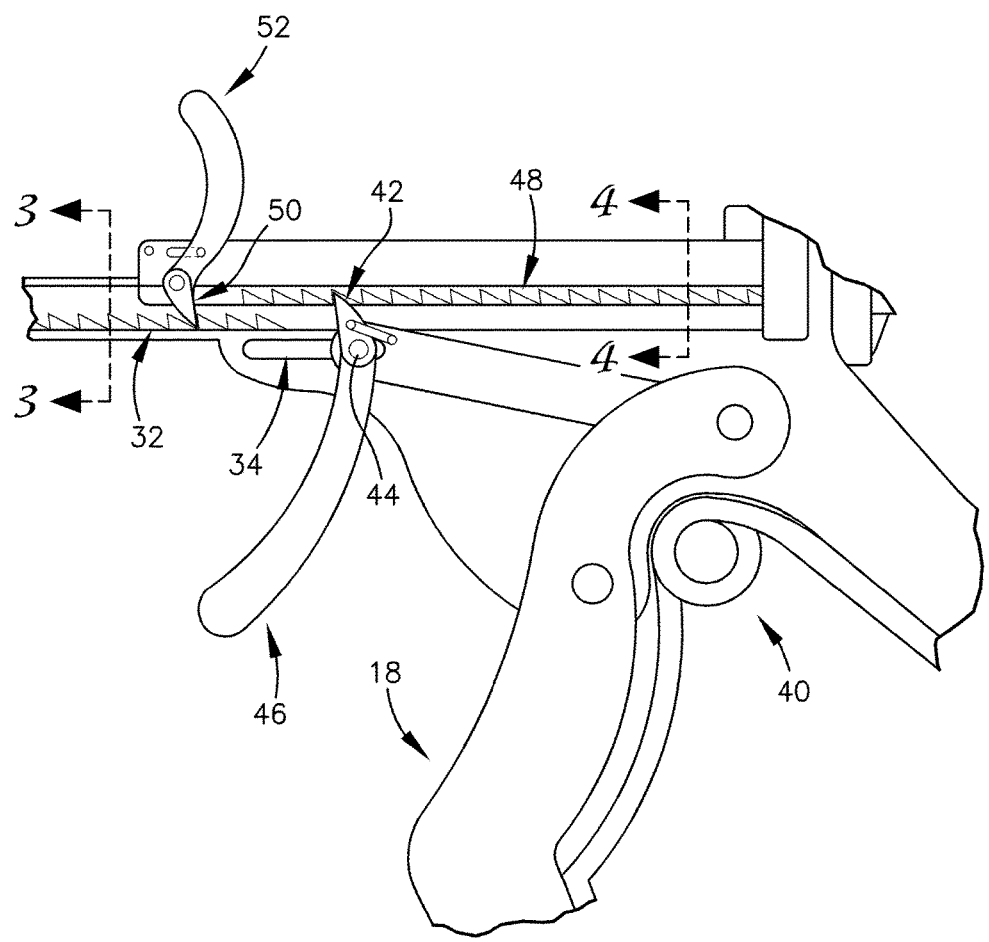
FIG. 2 is an enlarged side elevation view of a ratcheting mechanism of the articulating wire passer.
Figure 3:
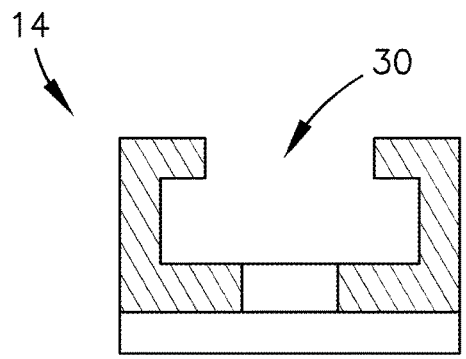
FIG. 3 is a sectional view of a channel of the articulating wire passer.
Figure 4:
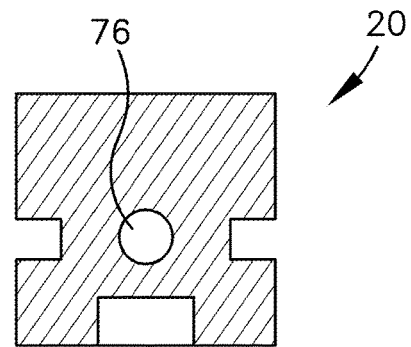
FIG. 4 is a sectional view of a push rod of the articulating wire passer.
Figure 5:
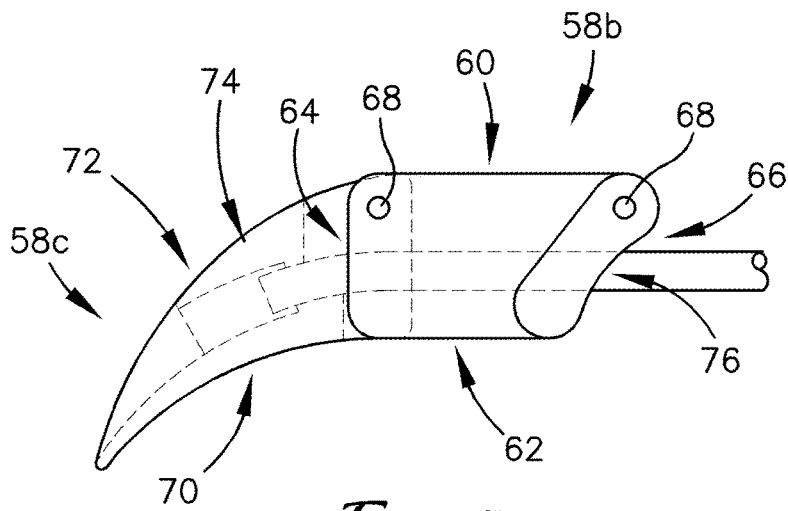
FIG. 5 is a side elevation view of segments of an articulable member of the articulating wire passer.
Figure 6:
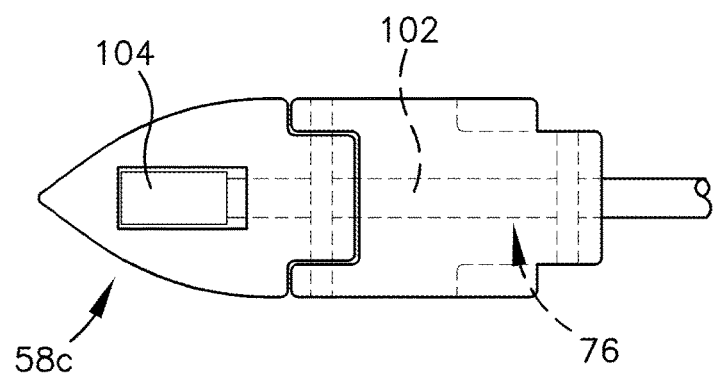
FIG. 6 is a top plan view of the segments of FIG. 5.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention may be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Turning now to the drawing figures, an articulating wire passer 10 is illustrated in accordance with embodiments of the invention. The articulating wire passer 10 broadly comprises a handle 12, a rigid guide section 14, a support guide 16, a trigger 18, a push rod 20, an articulable member 22, a tensioner 24, and a wire catcher 26.

The handle 12 allows a user to grip the articulating wire passer 10 and direct the articulable member 22 towards a bone 100. The handle 12 may have a pistol grip shape, a T-shape, or any other suitable shape and may have a protrusion 28, ergonomic gripping contours, ridges, or other geometry for allowing the user to firmly grasp the articulating wire passer 10.

The rigid guide section 14 extends forward from the handle 12 and may include a channel 30, a number of forward facing ratchet teeth 32, and a ratchet guide 34. The channel 30 guides the push rod 20 and articulable member 22 and may be enclosed or an open-topped U-shaped or C-shaped guide. The forward facing ratchet teeth 32 are aligned with the channel 30 for engaging a pawl of the push rod 20. The ratchet guide 34 is configured to receive a guide pin of a pawl of the trigger 18 and may be a groove, slot, cam, or similar feature for allowing the pawl of the trigger 18 to pivot into engagement with ratchet teeth of the push rod 20 and shift the push rod 20 forward.

The support guide 16 extends from a distal end of the rigid guide section 14 and may have a curved surface 36 for abutting the bone 100. The support guide 16 may also have a tip guide 38 for guiding the end segment of the articulable member 22 towards the wire catcher 26 after the end segment passes around the bone 100.

The trigger 18 allows the user to advance the articulable member 22 from an extended position to an engaged position and includes a return spring 40 and a pawl 42. The return spring 40 is connected between the trigger 18 and the handle 12 for urging the trigger 18 to a released position when a squeezing force is removed from the trigger 18 and handle 12. The return spring 40 may be a leaf spring, coil spring, torsion spring, or any other suitable spring. The pawl 42 is configured to ratchetably engage ratchet teeth of the push rod 20 and may include a guide pin 44 or similar feature for following the ratchet guide 34 of the rigid guide section 14 and a release 46 for disengaging the pawl 42 from the ratchet teeth of the push rod 20. The trigger 18 may be pivotably connected to the handle 12 near a top of the trigger 18 so as to form a fulcrum point such that the squeezing force urges the pawl 42 against the ratchet teeth of the push rod 20.

The push rod 20 may be an elongated member including a number of rear-facing ratchet teeth 48 and a pawl 50. The rear-facing ratchet teeth 48 are configured to be engaged by the pawl 42 of the trigger 18. The pawl 50 is configured to engage the forward-facing ratchet teeth 32 of the rigid guide section 14 and may include a release 52 for disengaging the pawl 50 from the forward-facing ratchet teeth 32. The push rod 20 may be pivotably connected to the first segment of the articulable member 22 at a distal end of the push rod 20 and may be slotted or otherwise shaped for being retained in the channel 30 of the rigid guide section 14.

The articulable member 22 guides the surgical wire 102 around the bone 100 and includes opposing aft and forward ends 54, 56. The articulable member 22 comprises a first end segment 58a, a number of intermediate segments 58b, and a second or distal end segment 58c (at least 5 segments, preferably at least 8 segments, and more preferably at least 10 segments in total) pivotably connected to each other. The segments 58a-c each include opposing top and bottom sides 60, 62 and opposing aft and forward ends 64, 66. The forward ends 66 are pivotably connected to aft ends 64 of adjacent segments 58a-c via pivot points 68 on the top sides 60 and may be indented or stepped for aligning with aft ends 64 of adjacent segments 58a-c and for pivoting relative to adjacent segments 58a-c a predetermined amount (at least 20 degrees, preferably at least 30 degrees, and more preferably at least 45 degrees). The first end segment 58a may be pivotably connected to the distal end of the push rod 20. The distal end segment 58c may have a concave curved bottom side 70 for following a convex contour of the bone 100 and a convex curved top side 72 such that the distal end segment 58c is tapered for allowing the articulable member 22 to be directed between the bone 100 and non-skeletal body mass near the bone 100. The end segment 58c may also be pointed for penetration through fascial tissues. The end segment 58c may also have end stopper engaging geometry 74 for retaining an end stopper 104 of the surgical wire 102 therein. The segments 58a-c may be slotted or otherwise shaped for being retained in the channel 30 of the rigid guide section 14. The segments 58a-c and the push rod 20 cooperatively form a longitudinal wire passageway 76 configured to receive the surgical wire 102 therein. The articulable member 22 is configured to be selectively shifted between an extended position and an engaged position as described in more detail below.

The tensioner 24 induces tension on the surgical wire 102 and may include a tensioning spring 78 and a wire lock 80. The tensioning spring 78 and/or tensioner 24 as a whole may be interchangeable for replacing a worn-out spring or for changing a tension force range of the articulating wire passer 10 for different applications. The wire lock 80 engages the surgical wire 102 and may be a pivotable friction cam, clamp, or other similar locking mechanism.

The wire catcher 26 includes a latch 82 configured to engage the end of the surgical wire 102 and a protrusion 84 for allowing the user to push the wire catcher 26 towards the tip guide 38 and pull the wire catcher 26 after it catches the surgical wire 102. The wire catcher 26 may be slideably attached to an underside of the rigid guide section 14 of the handle 12.

Use of the articulating wire passer 10 will now be described in more detail. First, the surgical wire 102 may be inserted through the wire passageway 76 of the push rod 20 and articulable member 22 such that the end stopper 104 of the surgical wire 102 is retained by the end stopper engaging geometry 74 of the end segment 58c. The tensioning spring 78 of the tensioner 24 may optionally be pre-compressed a desired amount. The wire lock 80 may then be shifted into engagement with the surgical wire 102. The articulating wire passer 10 may then be positioned such that the curved surface 52 of the support guide 18 rests against the bone 100.

The trigger 18 may then be squeezed such that the pawl 42 of the trigger 18 urges the push rod 20 and articulable member 22 forward a small amount (at least 0.25 inches, preferably at least 0.5 inches, and more preferably at least 1 inch) along the channel 30 of the rigid guide section 14 via the ratchet teeth 48 of the push rod 20. The pawl 50 of the push rod 20 passively slides over the ratchet teeth 32 of the rigid guide section 14 as the push rod 20 is moved forward and engages one of ratchet teeth 32 when the push rod 20 and articulable member 22 stop advancing, which prevents the push rod 20 and articulable member 22 from backtracking.

The end segment 58c of the articulable member 22 pulls the surgical wire 102 and hence the wire lock 80 forward via the end stopper engaging geometry 74. This compresses the tensioning spring 78, which induces or increases tension in the surgical wire 102. The tension in the surgical wire 102 causes segments (e.g., end segment 58c) to pivot relative to the next segment (e.g., adjacent segment 58b) around the bone 100 as they emerge from the distal end of the channel 30. The free segments may pivot to a predetermined relative angle (at least 20 degrees, preferably at least 30 degrees, and more preferably at least 45 degrees) dictated by the shape of the segments 58a-c or a desired relative angle according to a wire tension induced by the tensioner 24.

The trigger 18 may then be released such that the return spring 40 urges the trigger 18 back to a relaxed position. The pawl 42 of the trigger 18 passively slides over the ratchet teeth 48 of the push rod 20 as the trigger 18 returns to the relaxed position and engages one of the ratchet teeth 48 when the trigger 18 is stopped or reaches the relaxed position. The trigger 18 may be repeatedly squeezed and released such that the articulable member 22 curls around the bone 100 from an extended position to an engaged position as the articulable member 22 and push rod 20 are ratcheted forward.

The end segment 58c pierces and/or passes between soft tissues (such as the intermuscular septum of the thigh) and draws the surgical wire 102 around the bone 100 as the articulable member 22 advances. The end section 58*c* then advances along the tip guide 38 of the support guide 16 towards the wire catcher 26 on the other side of the bone 100.

The wire catcher 26 may then be shifted forward along the underside of the rigid guide section 14 until the latch 82 has moved past the end stopper 104 of the surgical wire 102. The wire catcher 26 may then be shifted backwards along the underside of the rigid guide section 14 such that the latch 82 engages the end stopper 104 of the surgical wire 102. Alternatively, the latch 82 may automatically engage the end stopper 104 when the wire catcher 26 is shifted forward.

The release 46 of the trigger 18 may be depressed or rotated to disengage the pawl 42 of the trigger 18 from the ratchet teeth 48 of the push rod 20 and the release 52 of the push rod 20 may be depressed or rotated to disengage the pawl 50 of the push rod 20 from the ratchet teeth 32 of the rigid guide section 14. The push rod 20 and articulable member 22 may then be shifted backwards towards the tensioner 24 such that the segments 58*a-c* shift back around the bone 100 from the engaged position to the extended position. The surgical wire 102 stays wrapped around the bone 100 because the end stopper 104 of the surgical wire 102 is in engagement with the latch 82 of the wire catcher 26. The surgical wire 102 may then be clipped between approximately 2 inches and 5 inches (depending on the diameter of the bone 100) from its end to form a wire piece. The wire piece may then be clamped to form a construct that encircles the bone, which can be used alone or in combination with plates, rods, or other methods of bone fixation. The articulating wire passer 10 may then be repositioned laterally along the bone 100 for passing additional surgical wire around the bone 100.

The above-described articulating wire passer 10 provides several advantages over conventional wire passers. For example, the articulating member 22 curls around the bone 100 due to tension in the surgical wire 102, thus ensuring that the disturbance of non-skeletal body mass near the bone 100 is minimized. The articulating wire passer 10 also allows the surgical wire 102 to be passed around the bone 100 without the handle 12 being moved significantly within the operating area. This reduces the surgical exposure and total space required to complete the surgery and reduces the likelihood of damaging non-skeletal body mass. The support guide 16 allows the user to position the articulating wire passer 10 against the bone 100 properly before passing the surgical wire 102 around the bone 100, which increases repeatability and accuracy of the procedure while decreasing the amount of time required to complete the surgery.

Although the invention has been described with reference to the exemplary embodiments illustrated in the attached drawings, it is noted that equivalents may be employed and substitutions made herein without departing from the scope of the invention as recited in the claims.

Having thus described various embodiments of the invention, what is claimed as new and desired to be protected by Letters Patent includes the following:

1. An articulating wire passer for passing a surgical wire around a bone, the articulating wire passer comprising:
 a handle configured to be gripped by a human hand; and
 an articulable member being slideable relative to the handle, the articulable member comprising
 at least five segments each having a top side including forward and aft pivot points and a bottom side opposite the top side,
 the segments being pivotably connected to each other via the pivot points,
 the segments forming at least a portion of a wire passageway for receiving at least a portion of the surgical wire therein such that the pivot points of the segments are offset from the wire passageway,
 the articulable member being shiftable between an extended position and an engaged position by pivoting the segments relative to each other at the pivot points via tension in the surgical wire.

2. The articulating wire passer of claim 1, wherein the articulable member is in ratcheting engagement with the handle.

3. The articulating wire passer of claim 1, further comprising a rigid guide section extending from the handle, the rigid guide section being configured to retain the segments of the articulable member in the extended position.

4. The articulating wire passer of claim 3, further comprising a support guide configured to be butted against the bone for properly positioning the wire passer before shifting the articulable member of the wire passer to the engaged position.

5. The articulating wire passer of claim 4, wherein the support guide includes a curved surface for following a convex contour of the bone.

6. The articulating wire passer of claim 1, further comprising a tensioner configured to selectively engage and induce tension in the surgical wire.

7. The articulating wire passer of claim 6, wherein the tensioner includes a wire lock configured to frictionally engage the surgical wire.

8. The articulating wire passer of claim 6, wherein the tensioner includes a coil spring.

9. The articulating wire passer of claim 1, wherein each segment includes an aft section and a forward section, the aft sections each being configured to overlap a forward section of an adjacent segment.

10. The articulating wire passer of claim 1, wherein the articulable member further comprises an end segment having a tapered end for allowing the articulable member to be directed between the bone and non-skeletal body mass near the bone.

11. The articulating wire passer of claim 10, wherein the end segment has a curved bottom side for following a convex contour of the bone.

12. A method of passing a surgical wire around a bone, the method comprising the steps of:
 (a) placing the surgical wire in a wire passageway of an articulating wire passer;
 (b) shifting an articulable member of the articulating wire passer from an extended position to an engaged position such that at least an end portion of the articulable member curls; and
 (c) simultaneously with step (b), extending the curling end portion of the articulable member around the bone, wherein said shifting of step (b) is caused by tensioning the surgical wire in the wire passageway.

13. The method of claim 12, wherein placing the surgical wire in the wire passageway of the wire passer includes positioning an end stopper of the surgical wire in an end segment of the articulable member so as to retain the surgical wire in the wire passageway.

14. The method of claim 12, wherein shifting the articulable member of the wire passer from the extended position to the engaged position includes ratcheting the articulable member relative to a handle of the wire passer.

15. The method of claim 12, further comprising selectively engaging the surgical wire by shifting a tensioner against the surgical wire.

16. The method of claim 12, further comprising engaging the bone via a support guide of the wire passer so as to properly position the wire passer against the bone before shifting the articulable member of the wire passer to the engaged position.

17. The method of claim 12, further comprising retrieving an end of the surgical wire and pulling the articulable member back around the bone such that the surgical wire remains encircling the bone.

18. The method of claim 17, wherein the step of retrieving the end of the surgical wire includes shifting a wire catcher towards an end of the articulable member when the articulable member is in the engaged position such that the wire catcher engages the end of the surgical wire.

19. The method of claim 17, further comprising the step of shifting the articulable member to the extended position after the wire catcher is engagement with the end of the surgical wire.

20. A method of passing a surgical wire around a bone, the method comprising the steps of:

(a) placing the surgical wire in a wire passageway of an articulating wire passer;
(b) positioning an end stopper of the surgical wire in an end segment of the articulable member so as to retain the surgical wire in the wire passageway;
(c) engaging the bone via a support guide of the articulating wire passer so as to properly position the wire passer against the bone;
(d) shifting a tensioner into frictional engagement with the surgical wire so as to induce tension in the surgical wire;
(e) ratcheting the articulable member towards the bone such that portions of the articulable member begin to curl due to the tension in the surgical wire as the portions become unrestricted from a handle of the wire passer so that the articulable member is shifted from an extended position to an engaged position;
(f) simultaneously with step (e), extending the curling end portion of the articulable member around the bone;
(g) retrieving an end of the surgical wire via a wire catcher; and
(h) pulling the articulable member back around the bone such that the surgical wire remains encircling the bone.

* * * * *